United States Patent
Xiao et al.

(10) Patent No.: US 10,319,584 B2
(45) Date of Patent: Jun. 11, 2019

(54) COMPOSITIONS AND PROCESSES FOR DEPOSITING CARBON-DOPED SILICON-CONTAINING FILMS

(71) Applicant: Air Products and Chemicals, Inc., Allentown, PA (US)

(72) Inventors: Manchao Xiao, San Diego, CA (US); Xinjian Lei, Vista, CA (US); Ronald Martin Pearlstein, San Marcos, CA (US); Haripin Chandra, San Marcos, CA (US); Eugene Jospeh Karwacki, Jr., Orefield, PA (US); Bing Han, San Marcos, CA (US); Mark Leonard O'Neill, Queen Creek, AZ (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 0 days.

(21) Appl. No.: 15/233,018

(22) Filed: Aug. 10, 2016

(65) Prior Publication Data

US 2016/0351389 A1 Dec. 1, 2016

Related U.S. Application Data

(62) Division of application No. 14/122,825, filed on Jun. 4, 2014, now Pat. No. 9,447,287.
(Continued)

(51) Int. Cl.
*H01L 21/02* (2006.01)
*C07F 7/10* (2006.01)
(Continued)

(52) U.S. Cl.
CPC ...... *H01L 21/02211* (2013.01); *C07F 7/0896* (2013.01); *C07F 7/10* (2013.01);
(Continued)

(58) Field of Classification Search
CPC ....................................................... C07F 7/10
See application file for complete search history.

(56) References Cited

U.S. PATENT DOCUMENTS

| 4,950,950 A | 8/1990 | Perry et al. |
| 4,988,573 A | 1/1991 | Nakayama et al. |

(Continued)

FOREIGN PATENT DOCUMENTS

| BE | 672101 A | 3/1966 |
| CN | 1834288 | 9/2006 |

(Continued)

OTHER PUBLICATIONS

Wang Organometallics 1991 V10 p. 2222-27 (Year: 1991).*
(Continued)

*Primary Examiner* — Joseph A Miller, Jr.
(74) *Attorney, Agent, or Firm* — Joseph D. Rossi

(57) ABSTRACT

Described herein are compositions for depositing a carbon-doped silicon containing film wherein the composition comprises a first precursor comprising at least one compound selected from the group consisting of: an organoaminoalkylsilane having a formula of $R^5Si(NR^3R^4)_xH_{3-x}$ wherein x=1, 2, 3; an organoalkoxyalkylsilane having a formula of $R^6Si(OR^7)_xH_{3-x}$ wherein x=1, 2, 3; an organoaminosilane having a formula of $R^8N(SiR^9(NR^{10}R^{11})H)_2$; an organoaminosilane having a formula of $R^8N(SiR^9LH)_2$ and combinations thereof; and optionally a second precursor comprising a compound having the formula: $Si(NR^1R^2)H_3$. Also described herein are methods for depositing a carbon-doped silicon-containing film using the composition wherein the method is one selected from the following: cyclic chemical vapor deposition (CCVD), atomic layer deposition (ALD), plasma enhanced ALD (PEALD) and plasma enhanced CCVD (PECCVD).

4 Claims, 4 Drawing Sheets

Related U.S. Application Data

(60) Provisional application No. 61/493,031, filed on Jun. 3, 2011.

(51) Int. Cl.

| | |
|---|---|
| *C07F 7/08* | (2006.01) |
| *C23C 16/30* | (2006.01) |
| *C23C 16/34* | (2006.01) |
| *C23C 16/40* | (2006.01) |
| *C23C 16/455* | (2006.01) |
| *C09D 5/00* | (2006.01) |
| *C09D 7/63* | (2018.01) |

(52) U.S. Cl.
CPC ............. *C09D 5/00* (2013.01); *C09D 7/63* (2018.01); *C23C 16/30* (2013.01); *C23C 16/345* (2013.01); *C23C 16/401* (2013.01); *C23C 16/45553* (2013.01); *H01L 21/0228* (2013.01); *H01L 21/02126* (2013.01)

(56) References Cited

U.S. PATENT DOCUMENTS

| | | | |
|---|---|---|---|
| 5,424,095 | A | 6/1995 | Clark et al. |
| 5,744,196 | A | 4/1998 | Laxman et al. |
| 5,888,662 | A | 3/1999 | Gorsuch et al. |
| 7,875,312 | B2 | 1/2011 | Thridandam et al. |
| 7,875,556 | B2 | 1/2011 | Xiao et al. |
| 7,932,413 | B2 | 4/2011 | Xiao et al. |
| 2002/0187644 | A1 | 12/2002 | Baum et al. |
| 2004/0052004 | A1 | 3/2004 | Nakayama |
| 2005/0287747 | A1 | 12/2005 | Chakravarti et al. |
| 2006/0045986 | A1 | 3/2006 | Hochberg |
| 2006/0228903 | A1 | 10/2006 | McSwiney et al. |
| 2006/0258173 | A1 | 11/2006 | Xiao |
| 2008/0124946 | A1 | 5/2008 | Xiao et al. |
| 2008/0207007 | A1 | 8/2008 | Thridandam et al. |
| 2010/0190348 | A1 | 7/2010 | Akae et al. |

FOREIGN PATENT DOCUMENTS

| | | |
|---|---|---|
| CN | 101255548 | 9/2008 |
| EP | 1785266 A1 | 5/2007 |
| EP | 1867687 A1 | 12/2007 |
| JP | 2265242 A | 10/1990 |
| JP | 2004103688 | 2/2004 |
| JP | 2008506262 | 2/2008 |
| JP | 2010118664 | 5/2010 |
| JP | 2010225663 | 10/2010 |
| JP | 2010267971 | 11/2010 |
| JP | 2010275602 A | 12/2010 |
| JP | 2010539730 | 12/2010 |
| KR | 1020030094310 | 11/2003 |
| KR | 1020100061733 | 8/2010 |
| WO | 02079211 A1 | 10/2002 |
| WO | 2008121463 A1 | 10/2008 |
| WO | 2010017869 A1 | 4/2010 |

OTHER PUBLICATIONS

A.M. Wrobel et al., "Reactivity of Organosilicon Precursors in Remote Hydrogen Microwave Plasma Chemical Vapor Deposition of Silicon Carbide and Silicon Carbonitride Thin-Film Coatings", Applied Organometallic Chemistry, vol. 24, No. 3, Mar. 1, 2010, pp. 201-207.

I. Blaszczyk-Lezak et al., "Silicon Carbonitride by Remote Microwave Plasma CVD From Organosilicon Precursor: Physical and Mechanical Properties of Deposited Si:C:N Films", Applied Surface Scienct, vol. 253, No. 18, Jun. 7, 2007, pp. 7404-7411.

E. Bacque et al., "Synthesis and Chemical Properties of 1,3-Dichloro-1,3-Dihydridodisilazanes", Journal of Organometallic Chemistry, vol. 481, Jan. 1, 1994, pp. 167-172.

H. Fleischer et al., "Gas-Phase Molecular Structures of Bis(Chloromethylsilyl)Amine and Bis(Chloromethylsilyl)Methylamine by Electron Diffraction and AB Initio Calculations; Experimental Support for n(N)-σ*(Si—Cl) Hyperconjugation‡", Journal of the the Chemical Society, No. 14, Jan. 1, 1998, pp. 593-600.

B. Arkles, "Silicon Nitride From Organosilazane Cyclic and Linear Prepolymers", Journal of the Electromechanical Society, vol. 133, No. 1, Jan. 1986, pp. 233-234.

\* cited by examiner

COMPOSITIONS AND PROCESSES FOR DEPOSITING CARBON-DOPED SILICON-CONTAINING FILMS

CROSS-REFERENCE TO RELATED APPLICATIONS

This application is a divisional application of U.S. application Ser. No. 14/122,825, filed Jun. 4, 2014. This application also claims the benefit of U.S. Application No. 61/493,031, filed on Jun. 3, 2011. The disclosure of application Ser. No. 14/122,825 and 61/493,031 are hereby incorporated by reference.

BACKGROUND OF THE INVENTION

Precursor(s), particularly organoaminosilane precursors, that can be used for the deposition of silicon containing films, including but not limited to, silicon oxide films, silicon nitride films, or silicon oxynitride films which further comprise carbon (referred to collectively herein as carbon-doped silicon-containing films) are described herein. In yet another aspect, described herein is the use of the organoaminosilane precursor(s) for depositing silicon-containing in the fabrication of devices, such as, but not limited to, integrated circuit devices. In these or other aspects, the organoaminosilane precursor(s) may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LP-CVD"), and atmospheric pressure chemical vapor deposition.

Several classes of compounds can be used as precursors for carbon-doped silicon-containing films. Examples of these compounds suitable for use as precursors include silanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

Some important characteristics of a carbon-doped silicon-containing film are wet etch resistance and hydrophobicity. Generally speaking, the introduction of carbon to a silicon-containing film helps decrease the wet etch rate and increases the hydrophobicity. Additional advantages of adding carbon to a silicon containing film is to lower the dielectric constant or provide improvements to other electrical or physical attributes of the film.

Further examples of precursors and processes for depositing carbon-doped silicon-containing films are provided in the following references. Applicants' patents, U.S. Pat. Nos. 7,875,556; 7,875,312; and U.S. Pat. No. 7,932,413, described classes of aminosilanes which are used for the deposition of dielectric films, such as, for example, silicon oxide and silicon carbonitride films in a chemical vapor deposition or atomic layer deposition process.

Japanese Publ. No. JP 2010/275602 describes a material for chemical vapor deposition for depositing a silicon-containing thin film that is represented by the formula HSiMe($R^1$)($NR^2R^3$) ($R^1$=$NR^4R^5$, C1-5 alkyl; $R^2$, $R^4$=H, C1-5 alkyl; $R^3$, $R^5$=C1-5 alkyl). The silicon-containing thin film is formed by temperatures ranging from 300-500° C.

US Publ. No. 2008/0124946A1 describes a process for depositing a carbon containing silicon oxide film, or a carbon containing silicon nitride film having enhanced etch resistance. The process comprises using a structure precursors containing silicon, a dopant precursor containing carbon, and mixing the dopant precursors with the structure precursor to obtain a mixture having a mixing ratio of Rm (% weight of the dopant precursor added to the structure precursor) between 2% and 85%; and a flow rate of Fm; providing a chemical modifier having a flow rate of Fc; having a flow ratio R2 defined as R2=Fm/Fc between 25% and 75%; and producing the carbon containing silicon containing film or the carbon containing silicon oxide film having enhanced etch resistance wherein the etch resistance is increased with increasing incorporation of the carbon.

US Publ. No. 2006/0228903 describes a process for fabricating a carbon doped silicon nitride layer using a first precursor which provides a source of silicon and a second precursor which adds carbon to the film. Examples of first precursor described in the '903 publication include halogenated silanes and disilanes, aminosilanes, cyclodisilazanes, linear and branched silizanes, azidosilanes, substituted versions of 1,2,4,5-tetraaza-3,6-disilacyclohexane, and silyl hydrazines. Examples of the second precursor described in the '903 publication are alkyl silanes that have the general formula $SiR_4$ where R is any ligand including but not limited to hydrogen, alkyl and aryl (all R groups are independent), alkyl polysilanes, halogenated alkyl silanes, carbon bridged silane precursors; and silyl ethanes/ethylene precursors.

US Publ. No. 2005/0287747A1 describes a process for forming a silicon nitride, silicon oxide, silicon oxynitride or silicon carbide film that includes adding at least one non-silicon precursor (such as a germanium precursor, a carbon precursor, etc.) to improve the deposition rate and/or makes possible tuning of properties of the film, such as tuning of the stress of the film.

U.S. Pat. No. 5,744,196A discloses the process comprises (a) heating a substrate upon which $SiO_2$ is to be deposited to approximately 150-500 Deg in a vacuum maintained at approximately 50-750 m torr; (b) introducing into the vacuum an organosilane-containing feed and an O-containing feed, the organosilane contg.-feed consisting essentially of >=1 compds. having the general formula $R^1Si(H_2)C_x$ $(R^4)_2 Si(H_2)R^2$, where $R^1$, $R^2$=C1-6 alkyl, alkenyl, alkynyl, or aryl, or $R^1$ and $R^2$ are combined to form an alkyl chain $Cx(R^3)_2$; $R^3$=H, $C_xH_{2x+1}$; x=1-6; $R^4$=H, $C_yH_{2y+1}$; and y=1-6; and (c) maintaining the temperature and vacuum, thereby causing a thin film of $SiO_2$ to deposit on the substrate.

Precursors and processes that are used in depositing carbon-doped silicon oxide films generally deposit the films at temperatures greater than 550° C. The trend of miniaturization of semiconductor devices and low thermal budget requires lower process temperatures and higher deposition rates. Further, there is a need in the art to provide novel precursors or combinations of precursors that may allow for more effective control of the carbon content contained in the carbon-doped silicon containing film. Accordingly, there is a continuing need in the art to provide compositions of precursors for the deposition of carbon-doped silicon-containing films which provide films that exhibit one or more of the following attributes: lower relative etch rates, greater hydrophobicity, higher deposition rates, higher density, compared to films deposited using the individual precursors alone.

BRIEF SUMMARY OF THE INVENTION

Described herein are precursor compositions and methods using same for forming films comprising carbon-doped silicon (referred to herein as silicon containing films), such as, but not limited to, carbon-doped stoichiometric or non-stoichiometric silicon oxide, carbon-doped stoichiometric or non-stoichiometric silicon nitride, silicon oxynitride, silicon oxycarbide, silicon carbonitride, and combinations thereof onto at least a portion of a substrate. In certain embodiments, the carbon-doped silicon-containing can have a carbon content of $2 \times 10^{19}$ carbon atom/cc or less of carbon as measured by measured by dynamic Secondary Ions Mass Spectrometry (SIMS). In alternative embodiments, the carbon-doped silicon-containing films can have a carbon content that ranges from about $2 \times 10^{19}$ carbon atom/cc to $2 \times 10^{22}$ carbon atom/cc as measured by dynamic SIMS.

Also described herein are the methods to form carbon-doped silicon containing films or coatings on an object to be processed, such as, for example, a semiconductor wafer. In one embodiment of the method described herein, a layer comprising silicon, carbon and oxygen is deposited onto a substrate using the precursor composition described herein and an oxidizing agent in a deposition chamber under conditions for generating a carbon-doped silicon oxide layer on the substrate. In another embodiment of the method described herein, a layer comprising silicon, carbon, and nitrogen is deposited onto a substrate using the precursor composition described herein and an nitrogen containing precursor in a deposition chamber under conditions for generating a carbon-doped silicon nitride layer on the substrate. In certain embodiments, the deposition method for depositing the carbon-doped silicon-containing film using the precursor composition described herein is selected from the group consisting of cyclic chemical vapor deposition (CCVD), atomic layer deposition (ALD), plasma enhanced ALD (PEALD) and plasma enhanced CCVD (PECCVD).

In one aspect, there is provided a composition for depositing a carbon-doped silicon containing film comprising:

(a) a first precursor comprising at least one selected from the group consisting of:
 (i) an organoaminoalkylsilane having a formula of $R^5Si(NR^3R^4)_xH_{3-x}$ wherein x=1, 2, 3;
 (ii) an organoalkoxyalkylsilane having a formula of $R^6Si(OR^7)_xH_{3-x}$ wherein x=1, 2, 3;
 (iii) an organoaminosilane having a formula of $R^8N(SiR^9(NR^{10}R^{11})H)_2$;
 (iv) an organoaminosilane having a formula of $R^8N(SiR^9LH)_2$; and combinations thereof;
wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and L=Cl, Br, or I; wherein $R^3$ and $R^4$ can form a cyclic ring or an alkyl-substituted cyclic ring; and wherein $R^{10}$ and $R^{11}$ can form a cyclic ring or an alkyl-substituted cyclic ring; and (b) optionally a second precursor comprising an organoaminosilane having a formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring.

In a further aspect, there is provided a composition for depositing a carbon-doped silicon containing film comprising:

a first precursor comprising at least one selected from the group consisting of:
 an organoaminoalkylsilane having a formula of $R^5Si(NR^3R^4)_xH_{3-x}$ wherein x=1, 2, 3;
 an organoalkoxyalkylsilane having a formula of $R^6Si(OR^7)_xH_{3-x}$ wherein x=1, 2, 3;
 an organoaminosilane having a formula of $R^8N(SiR^9(NR^{10}R^{11})H)_2$;
 an organoaminosilane having a formula of $R^8N(SiR^9LH)_2$; and combinations thereof;
wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and L=Cl, Br, or I; wherein $R^3$ and $R^4$ can form a cyclic ring or an alkyl-substituted cyclic ring; and wherein $R^{10}$ and $R^{11}$ can form a cyclic ring or an alkyl-substituted cyclic ring; and optionally a second precursor comprising an organoaminosilane having a formula of $R^{12}Si(NR^{13}R^{14})_xH_{3-x}$ wherein x=0, 1, 2, 3, and 4, wherein $R^{12}$, $R^{13}$, and $R^{14}$ are each independently selected from the group consisting of H, a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^{13}$ and $R^{14}$ can form a cyclic ring or an alkyl-substituted cyclic ring.

In another aspect, there is provided a composition for depositing a carbon-doped silicon containing film comprising: a first precursor comprising an organoaminoalkylsilane having a formula of $R^5Si(NR^3R^4)_xH_{3-x}$ wherein x=1, 2, 3 wherein $R^3$ and $R^4$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ is selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and a halide atom, and wherein $R^3$ and $R^4$ can form a cyclic ring or an alkyl-substituted cyclic ring. In this or other embodiments, the composition further comprises a second precursor comprising an organoaminosilane having a formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring.

In a further aspect, there is provided a composition for depositing a carbon-doped silicon containing film comprising: a first precursor comprising: an organoalkoxyalkylsilane having a formula of $R^6Si(OR^7)_xH_{3-x}$ wherein x=1, 2, 3 and wherein $R^7$ is independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^6$ is independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group. In this or other embodiments, the composition further comprises a second precursor comprising an organoaminosilane having a formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring.

In yet another aspect, there is provided a composition for depositing a carbon-doped silicon containing film comprising: a first precursor comprising: an organoaminosilane having a formula of $R^8N(SiR^9(NR^{10}R^{11})H)_2$ wherein $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and wherein $R^{10}$ and $R^{11}$ can form a cyclic ring or an alkyl-substituted cyclic ring. In this or other embodiments, the composition further comprises a second precursor comprising an organoaminosilane having a formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring.

In another aspect, there is provided a method of forming a carbon-doped silicon oxide film via an atomic layer deposition process, the method comprising the steps of:
  a. providing a substrate in a reactor;
  b. introducing into the reactor a first precursor comprising at least one compound selected from the group consisting of:
    (i) an organoaminoalkylsilane having a formula of $R^5Si(NR^3R^4)_xH_{3-x}$ wherein x=1, 2, 3;
    (ii) an organoalkoxyalkylsilane having a formula of $R^6Si(OR^7)_xH_{3-x}$ wherein x=1, 2, 3;
    (iii) an organoaminosilane having a formula of $R^8N(SiR^9(NR^{10}R^{11})H)_2$;
    (iv) an organoaminosilane having a formula of $R^8N(SiR^9LH)_2$ and combinations thereof;
  wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; L=Cl, Br, or I and wherein $R^3$ and $R^4$ can form a cyclic ring or an alkyl-substituted cyclic ring; and wherein $R^{10}$ and $R^{11}$ can form a cyclic ring or an alkyl-substituted cyclic ring;
  c. purging the reactor with a purge gas;
  d. introducing an oxygen source into the reactor;
  e. introducing into the reactor a second precursor having the following formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring;
  f. purging the reactor with a purge gas;
  g. introducing an oxygen source into the reactor;
  h. purging the reactor with a purge gas; and
  i. repeating the steps b through h until a desired thickness of the film is obtained. In one particular embodiment of the method described herein, the precursor in step (b) comprises an organoaminoalkylsilane described herein as (i). More particularly, the precursor in step (b) comprises the organaoaminoalkylsilane 2,6-dimethylpiperidinomethylsilane.

In another aspect, there is provided a method of forming a carbon-doped silicon nitride film via an atomic layer deposition process, the method comprising the steps of:
 a. providing a substrate in a reactor;
 b. introducing into the reactor a first precursor comprising at least one compound selected from the group consisting of:
  (i) an organoaminoalkylsilane having a formula of $R^5Si(NR^3R^4)_xH_{3-x}$ wherein x=1, 2, 3;
  (ii) an organoalkoxyalkylsilane having a formula of $R^6Si(OR^7)_xH_{3-x}$ wherein x=1, 2, 3;
  (iii) an organoaminosilane having a formula of $R^8N(SiR^9(NR^{10}R^{11})H)_2$;
  (iv) an organoaminosilane having a formula of $R^8N(SiR^9LH)_2$ and combinations thereof;
wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; L=Cl, Br, or I and wherein $R^3$ and $R^4$ can form a cyclic ring or an alkyl-substituted cyclic ring; and wherein $R^{10}$ and $R^{11}$ can form a cyclic ring or an alkyl-substituted cyclic ring;
 c. purging the reactor with a purge gas;
 d. introducing a nitrogen source into the reactor;
 e. introducing into the reactor a second precursor having the following formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring
 f. purging the reactor with a purge gas;
 g. introducing a nitrogen source into the reactor;
 h. purging the reactor with a purge gas; and
 i. repeating the steps b through h until a desired thickness of the film is obtained. In one particular embodiment of the method described herein, the precursor in step (b) comprises an organoaminoalkylsilane described herein as (i). More particularly, the precursor in step (b) comprises the organaoaminoalkylsilane 2,6-dimethylpiperidinomethylsilane.

In another aspect, there is provided a method of forming a carbon-doped silicon oxide film via an atomic layer deposition process, the method comprising the steps of:
 a. providing a substrate in a reactor;
 b. introducing into the reactor a first precursor comprising at least one compound selected from the group consisting of:
  (v) an organoaminoalkylsilane having a formula of $R^5Si(NR^3R^4)_xH_{3-x}$ wherein x=1, 2, 3;
  (vi) an organoalkoxyalkylsilane having a formula of $R^6Si(OR^7)_xH_{3-x}$ wherein x=1, 2, 3;
  (vii) an organoaminosilane having a formula of $R^8N(SiR^9(NR^{10}R^{11})H)_2$;
  (viii) an organoaminosilane having a formula of $R^8N(SiR^9LH)_2$ and combinations thereof;
wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; L=Cl, Br, or I and wherein $R^3$ and $R^4$ can form a cyclic ring or an alkyl-substituted cyclic ring; and wherein $R^{10}$ and $R^{11}$ can form a cyclic ring or an alkyl-substituted cyclic ring;
 c. purging the reactor with a purge gas;
 d. introducing an oxygen source into the reactor;
 e. introducing into the reactor a second precursor having a formula of $R^{12}Si(NR^{13}R^{14})_xH_{3-x}$ wherein x=0, 1, 2, 3, and 4, wherein $R^{12}$, $R^{13}$, and $R^{14}$ are each independently selected from the group consisting of H, a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^{13}$ and $R^{14}$ can form a cyclic ring or an alkyl-substituted cyclic ring;
 f. purging the reactor with a purge gas;
 g. introducing an oxygen source into the reactor;
 h. purging the reactor with a purge gas; and
 i. repeating the steps b through h until a desired thickness of the film is obtained. In one particular embodiment of the method described herein, the precursor in step (b) comprises an organoaminoalkylsilane described herein as (i). More particularly, the precursor in step (b) comprises the organaoaminoalkylsilane 2,6-dimethylpiperidinomethylsilane.

In another aspect, there is provided a method of forming a carbon-doped silicon nitride film via an atomic layer deposition process, the method comprising the steps of:
 a. providing a substrate in a reactor;

b. introducing into the reactor a first precursor comprising at least one compound selected from the group consisting of:
   (v) an organoaminoalkylsilane having a formula of $R^5Si(NR^3R^4)_xH_{3-x}$ wherein x=1, 2, 3;
   (vi) an organoalkoxyalkylsilane having a formula of $R^6Si(OR^7)_xH_{3-x}$ wherein x=1, 2, 3;
   (vii) an organoaminosilane having a formula of $R^8N(SiR^9(NR^{10}R^{11})H)_2$;
   (viii) an organoaminosilane having a formula of $R^8N(SiR^9LH)_2$ and combinations thereof;
wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; L=Cl, Br, or I and wherein $R^3$ and $R^4$ can form a cyclic ring or an alkyl-substituted cyclic ring; and wherein $R^{10}$ and $R^{11}$ can form a cyclic ring or an alkyl-substituted cyclic ring;
   c. purging the reactor with a purge gas;
   d. introducing a nitrogen source into the reactor;
   e. introducing into the reactor a second precursor having a formula of $R^{12}Si(NR^{13}R^{14})_xH_{3-x}$ wherein x=0, 1, 2, 3, and 4, wherein $R^{12}$, $R^{13}$, and $R^{14}$ are each independently selected from the group consisting of H, a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^{13}$ and $R^{14}$ can form a cyclic ring or an alkyl-substituted cyclic ring;
   f. purging the reactor with a purge gas;
   g. introducing a nitrogen source into the reactor;
   h. purging the reactor with a purge gas; and
   i. repeating the steps b through h until a desired thickness of the film is obtained. In one particular embodiment of the method described herein, the precursor in step (b) comprises an organoaminoalkylsilane described herein as (i). More particularly, the precursor in step (b) comprises the organaoaminoalkylsilane 2,6-dimethylpiperidinomethylsilane.

DETAILED DESCRIPTION OF THE INVENTION

Figure 1:
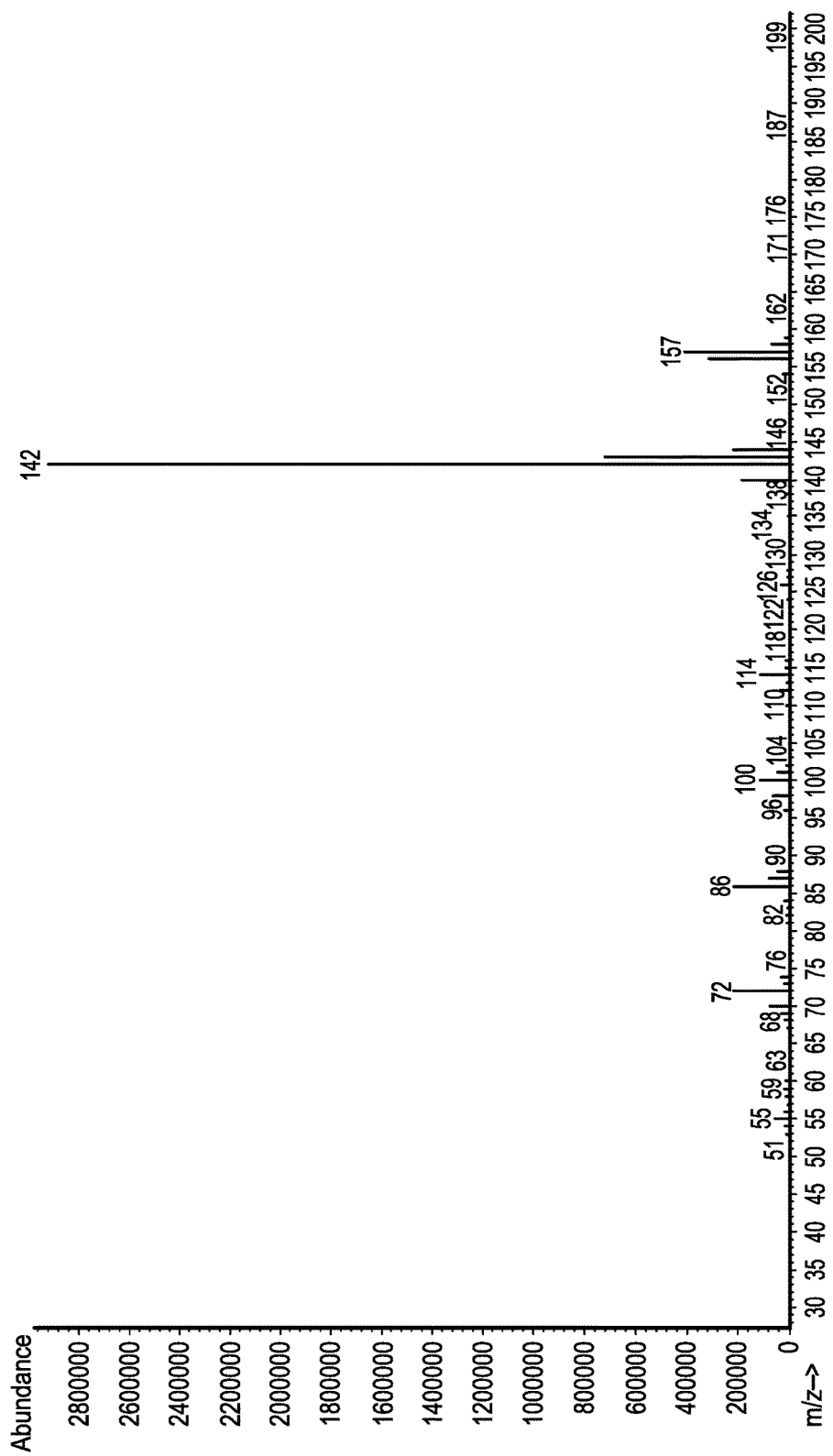
FIG. 1 provides the mass spectroscopy (MS) spectrum of 2,6-dimethylpiperidinomethylsilane described in Example 1.

Described herein are compositions comprising one or more precursors and processes for depositing a carbon-doped silicon-containing film via atomic layer deposition (ALD), cyclic chemical vapor deposition (CCVD) or plasma enhanced ALD (PEALD) or plasma enhanced CCVD (PECCVD) using the precursor compositions. The compositions described herein are comprised of, consist essentially of, or consist of, a first precursor comprising at least one compound selected from the group of compounds having the following formulas: (i) $R^5Si(NR^3R^4)_xH_{3-x}$; (ii) $R^6Si(OR^7)_xH_{3-x}$; (iii) an organoaminosilane having a formula of $R^8N(SiR^9(NR^{10}R^{11})H)_2$; and combinations of (i), (ii), and (iii) wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; and x=1, 2, or 3, and wherein $R^3$ and $R^4$ can form a cyclic ring or an alkyl-substituted cyclic ring; and wherein $R^{10}$ and $R^{11}$ can form a cyclic ring or an alkyl-substituted cyclic ring. In certain embodiments, the composition further comprises a second precursor comprising an organoaminosilane having a formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring.

The precursors in the composition described herein are typically high purity volatile liquid precursor chemical that are vaporized and delivered to a deposition chamber or reactor as a gas to deposit a silicon containing film via CVD or ALD processes for semiconductor or other devices. The selection of precursor materials for deposition depends upon the desired resultant dielectric material or film. For example, a precursor material may be chosen for its content of chemical elements, its stoichiometric ratios of the chemical elements, and/or the resultant silicon containing film or coating that are formed under CVD. The precursor material used in the compositions may also be chosen for various other characteristics such as cost, relatively low toxicity, handling characteristics, ability to maintain liquid phase at room temperature, volatility, molecular weight, and/or other considerations. In certain embodiments, the precursors in the composition described herein can be delivered to the reactor system by any number of means, preferably using a pressurizable stainless steel vessel fitted with the proper valves and fittings, to allow the delivery of liquid phase precursor to the deposition chamber or reactor.

The precursors in the compositions described herein exhibits a balance of reactivity and stability that makes them ideally suitable as CVD or ALD precursors. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor to prevent condensation or particles from forming in the container, lines, or both. With regard to stability, other organosilane precursors may form silane ($SiH_4$) as they degrade. Silane is pyrophoric at room temperature or it can spontaneously combust which presents safety and handling issues. Moreover, the formation of silane and other by-products decreases the purity level of the precursor and changes as small as 1 to 2% in chemical purity may be considered unacceptable for reliable semiconductor manufacture. In certain embodiments, the precursors in the compositions described herein comprise less than 2% by weight, or less than 1% by weight, or less than 0.5% by weight of by-product (such as the corresponding bis-silane byproduct) after being stored for a 6 months or greater, or one year or greater time period which is indicative of being shelf stable. In addition to the foregoing advantages, in certain embodiments, such as for depositing a silicon oxide or silicon nitride film using an ALD or PEALD deposition method, the organoaminosilane precursor described herein may be able to deposit high density materials at relatively low deposition temperatures, e.g., 500° C. or less, or 400° C. or less, 300° C. or less, 200° C. or less, 100° C. or less, or 50° C. or less. In certain embodiments, the composition described herein can deposit the carbon-doped silicon containing film at a deposition temperature of about 250° C. or less, 200° C. or less, 100° C. or less, or 50° C. or less.

The compositions described herein are used to deposit carbon-doped silicon-containing film that exhibit a higher wet etch resistance and a lower hydrophobicity compared to silicon-containing films that do not contain carbon. Not being bound by theory, the introduction of carbon to a silicon-containing film, particularly in lower alkyl forms (e.g., Me, Et, Pr, groups), helps decrease the wet etch rate and increases the hydrophobicity. Selective etching is particularly important in semiconductor patterning process. Additional advantages of adding carbon to a silicon containing film is to lower the dielectric constant or other electrical or physical attributes of the film. It is believed that the strength of the Si—C bond formed from the lower alkyl substituents on silicon, particularly the silicon-methyl bond, is sufficient for it to remain at least partially intact during film formation according to the processes described in this invention. The residual organic carbon in the silicon-containing film imparts reduced dielectric constant and enhances hydrophobicity and also reduces the etch rate using dilute aqueous hydrofluoric acid.

As previously discussed, the compositions described herein contain at least one precursors comprising an organic group, a nitrogen atom and a silicon atom. The first precursor is comprised of at least one compound selected from the compounds having the following formulas: (i) $R^5Si(NR^3R^4)_xH_{3-x}$, (ii) $R^6Si(OR^7)_xH_{3-x}$, (iii) $R^8N(SiR^9(NR^{10}R^{11})H)_2$ and combinations thereof. In certain embodiments, the precursors described herein alone or in combination, are delivered via a liquid injection apparatus. The carbon content in the resulting films can be adjusted by one or more of the following: the amount of carbon contained in the precursor, the type of carbon contained in the precursor, deposition conditions, in certain embodiments, the number of cycles of the first precursor relative to the number of cycles of the second precursor in a cyclic CVD or ALD process, in certain embodiments, the ratio of first precursor to second precursor in the composition, or combinations thereof.

In one embodiment, the composition for depositing a carbon-doped silicon containing film comprises a first precursor(s) comprising an organoaminoalkylsilane having a formula of $R^5Si(NR^3R^4)_xH_{3-x}$ wherein x=1, 2, 3 and wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ is selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and a halide atom; and wherein $R^3$ and $R^4$ can form a cyclic ring or an alkyl-substituted cyclic. In certain embodiments of the organoaminoalkylsilane having a formula of $R^5Si(NR^3R^4)_xH_{3-x}$, $R^3$ and $R^4$ can be combined to form a cyclic group. In these embodiments, the cyclic group may be a carbocyclic or heterocyclic group. The cyclic group can be saturated or, alternatively, unsaturated. In other embodiments of the oragnoaminoalkylsilane having a formula of $R^5Si(NR^3R^4)_xH_{3-x}$, $R^3$ and $R^4$ are not combined to form a cyclic group.

In another embodiment, the composition for depositing a carbon-doped silicon containing film comprises a first precursor(s) comprising an organoalkoxyalkylsilane having a formula of $R^6Si(OR^7)_xH_{3-x}$ wherein x=1, 2, 3 and wherein $R^7$ is selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; and $R^6$ is selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group, and a halide atom.

In a further embodiment, the composition for depositing a carbon-doped silicon containing film comprises a first precursor(s) comprising an organoaminosilane having a formula of $R^8N(SiR^9(NR^{10}R^{11})H)_2$ wherein $R^8$ and $R^9$ are each independently selected from the group consisting of hydrogen, $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; and wherein $R^{10}$ and $R^{11}$ can form a cyclic ring or an alkyl-substituted cyclic ring. In certain embodiments of the organoaminosilane having a formula of $R^8N(SiR^9(NR^{10}R^{11})H)_2$, $R^{10}$ and $R^{11}$ can be combined to form a cyclic group. In these embodiments, the cyclic group may be a carbocyclic or heterocyclic group. The cyclic group can be saturated or, alternatively, unsaturated. In other embodiments of the organoaminosilane having a formula of $R^8N(SiR^9(NR^{10}R^{11})H)_2$, $R^{10}$ and $R^{11}$ are not combined to form a cyclic group.

In another embodiment, the first precursor comprises an organoaminosilane with a formula of $R^8N(SiR^9LH)_2$ wherein $R^8$ and $R^9$ are independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group; and L is a halide selected from the group consisting of Cl, Br, I.

In certain embodiments, the composition for depositing a carbon-doped silicon containing film further comprises a second precursor comprising an organoaminosilane having a formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_3$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring. In certain embodiments of the organoaminosilane having formula $Si(NR^1R^2)H_3$, $R^1$ and $R^2$ can be linked together to form a ring. In these or other embodiments, the ring comprises a heterocyclic ring. The ring, or alternatively, heterocyclic ring, may be saturated or unsaturated. In alternative embodiments of the organoaminosilane having formula $Si(NR^1R^2)H_3$, $R^1$ and $R^2$ are not linked together to form a ring.

In an alternative embodiment, the optional second precursor can comprise an organoaminoalkylsilane having a formula of $R^{12}Si(NR^{13}R^{14})_xH_{3-x}$ wherein x=0, 1, 2, 3, and 4, wherein $R^{12}$, $R^{13}$, and $R^{14}$ are each independently selected from the group consisting of H, a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group. In certain embodiments of having formula, $R^{13}$ and $R^{14}$ can be linked together to form a ring. In these or other embodiments, the ring comprises a heterocyclic ring. The ring, or alternatively, heterocyclic ring, may be saturated or unsaturated. In alternative embodiments of the organoaminosilane having formula, $R^{13}$ and $R^{14}$ are not linked together to form a ring.

In the foregoing formulas for the first and second precursors and throughout the description, the term "alkyl" denotes a linear or branched functional group having from 1 to 10, or 3 to 10, or 1 to 6 carbon atoms. Exemplary linear alkyl groups include, but are not limited to, methyl, ethyl, propyl, butyl, pentyl, and hexyl groups. Exemplary branched alkyl groups include, but are not limited to, isopropyl, isobutyl, sec-butyl, tert-butyl, iso-pentyl, tert-pentyl, isohexyl, and neohexyl. In certain embodiments, the alkyl group may have one or more functional groups such as, but not limited to, an alkyl group, an alkoxy group, a dialkylamino group or combinations thereof, attached thereto. In other embodiments, the alkyl group does not have one or more functional groups attached thereto. The alkyl group may be saturated or, alternatively, unsaturated.

In the foregoing formulas and throughout the description, the term "cyclic alkyl" denotes a cyclic group having from 3 to 10 or 5 to 10 atoms. Exemplary cyclic alkyl groups include, but are not limited to, cyclobutyl, cyclopentyl, cyclohexyl, and cyclooctyl groups. In certain embodiments, the cyclic alkyl group may have one or more $C_1$ to $C_{10}$ linear, branched substituents, or substituents containing oxygen or nitrogen atoms. In this or other embodiments, the cyclic alkyl group may have one or more linear or branched alkyls or alkoxy groups as substituents, such as, for example, a methylcyclohexyl group or a methoxycyclohexyl group In the foregoing formulas and throughout the description, the term "aryl" denotes an aromatic cyclic functional group having from 5 to 10 carbon atoms or from 6 to 10 carbon atoms. Exemplary aryl groups include, but are not limited to, phenyl, benzyl, chlorobenzyl, tolyl, and o-xylyl.

In the foregoing formulas and throughout the description, the term "alkenyl group" denotes a group which has one or more carbon-carbon double bonds and has from 2 to 20 or from 2 to 10 or from 2 to 6 carbon atoms.

In the foregoing formulas and throughout the description, the term "alkynyl group" denotes a group which has one or more carbon-carbon triple bonds and has from 2 to 20 or from 2 to 10 or from 2 to 6 carbon atoms.

In the foregoing formulas and through the description, the term "unsaturated" as used herein means that the functional group, substituent, ring or bridge has one or more carbon double or triple bonds. An example of an unsaturated ring can be, without limitation, an aromatic ring such as a phenyl ring. The term "saturated" means that the functional group, substituent, ring or bridge does not have one or more double or triple bonds.

In certain embodiments, the term "carbocyclic or heterocyclic ring" denotes a carbocyclic or heterocyclic ring. Exemplary cyclic or alkyl substituted cyclic ring groups include, but not limited to, cyclohexyl, cyclopentyl, pyrrolidino, piperidino, morpholino, 2,5-dimethylpyrrolidino, 2,6-dimethylpiperidino, or other alkyl-substituted derivatives.

In certain embodiments, one or more of the alkyl group, alkenyl group, alkynyl group, aryl group, and/or aromatic group in the foregoing formulas may be substituted or have one or more atoms or group of atoms substituted in place of, for example, a hydrogen atom. Exemplary substituents include, but are not limited to, oxygen, sulfur, halide atoms (e.g., F, Cl, I, or Br), nitrogen, and phosphorous. In other embodiments, one or more of the alkyl group, alkenyl group, alkynyl group, alkoxyalkyl group, alkoxy group, alkylaminoalkyl group, aromatic and/or aryl group in the foregoing formulas may be unsubstituted.

Some specific examples of methyl-substituted compounds which can be used as the first precursor in the compositions described herein include, without limitation, bis(dimethylamino)methylsilane, diethylaminomethylsilane, t-butylaminomethylsilane, and isopropylaminomethylsilane.

In certain embodiments, the first precursor, second precursor, or both having the foregoing formulas has one or more substituents comprising oxygen atoms. In these embodiments, the need for an oxygen source during the deposition process may be avoided. In other embodiments, the first precursor, second precursor, or both having the foregoing formulas have one or more substituents comprising oxygen atoms also uses an oxygen source.

In certain embodiments, the composition described herein comprises a first precursor or organoaminoalkylsilane having the formula $R^5Si(NR^3R^4)_xH_{3-x}$ wherein x=1, 2, 3 and $R^3$, $R^4$, and $R^5$ are the substituents described herein. The organoaminoalkylsilane having the formula $R^5Si(NR^3R^4)_xH_{3-x}$ can be prepared by reacting an alkyl amine, $R^3R^4NH$, with a halosilane or an aminosilane in an organic solvent or solvent mixture with removal of hydrogen halide, or amine. The hydrogen halide may be conveniently removed by precipitation upon adding a tertiary amine and forming the corresponding amine hydrochloride salt. In one embodiment, an organoaminoalkylsilane having the formula $R^5Si(NR^3R^4)_xH_{3-x}$ wherein x=1 and $R^5$=Cl can be prepared, for example, in the reaction represented by Equation (1) below and $R^3$, Ware the substituents described herein:

In certain embodiments, the composition described herein comprises a first precursor or organoaminoalkylsilane having the formula $R^5Si(NR^3R^4)_xH_{3-x}$ wherein x=1, 2, 3 and $R^3$, $R^4$, and $R^5$ are the substituents described herein. The organoaminoalkylsilane having the formula $R^5Si(NR^3R^4)_xH_{3-x}$ can be prepared by reacting an alkyl amine, $R^3R^4NH$, with a halosilane or an aminosilane in an organic solvent or solvent mixture with removal of hydrogen halide or amine. The hydrogen halide may be conveniently removed by precipitation upon adding a tertiary amine and forming the corresponding amine hydrochloride salt. In one embodiment, an organoaminoalkylsilane having the formula $R^5Si(NR^3R^4)_xH_{3-x}$ wherein x=1 and $R^5$=Cl can be prepared, for example, in the reaction represented by Equation (1) below and $R^3$, $R^4$ are the substituents described herein:

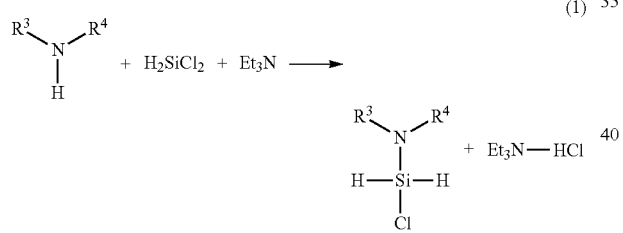

(1)

Another organoaminoalkylsilane having the formula, $R^5Si(NR^3R^4)_xH_{3-x}$ wherein x=1 and $R^5$ is a $C_1$ to $C_{10}$ linear or branched alkyl can be prepared, for example, in the reaction represented by Equation (2) below and $R^3$, $R^4$, and $R^5$ are the substituents described herein:

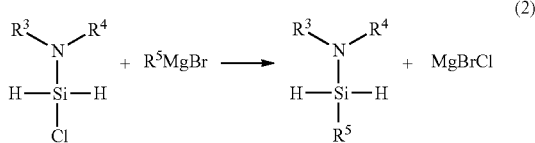

(2)

In another embodiment, the composition described herein comprises a first precursor having the formula $R^8N(SiR^9(NR^{10}R^{11})H)_2$ wherein $R^8$, $R^9$, $R^{10}$ and $R^{11}$ are substituent described herein. In one particular embodiment of the foregoing formula, $R^9$ is hydrogen, and the compound can be prepared, for example, in a method described in the following Equation 3 and 4 below and wherein $R^8$, $R^9$, $R^{10}$ and $R^{11}$ are substituent described herein:

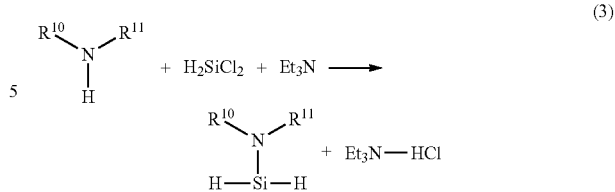

(3)

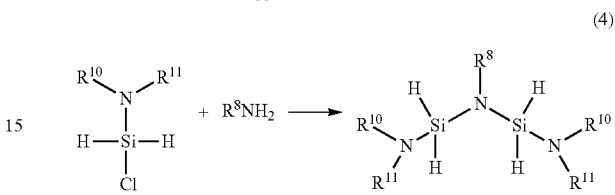

(4)

In yet another embodiment, the first precursor comprises an organoaminosilane having a formula of $R^8N(SiR^9LH)_2$ wherein $R^8$ and $R^9$ are the substituents described herein and L=Cl, Br, I. In one particular embodiment of the foregoing formula wherein L=Cl, the organoaminosilanes can be prepared, for example, in a method described in following Equation 5 below and wherein $R^8$ and $R^9$ are substituent described herein:

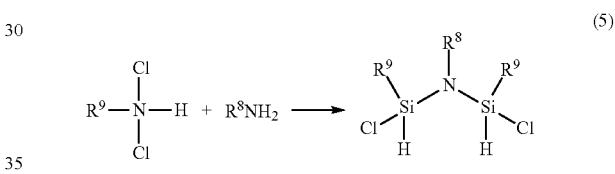

(5)

In embodiments wherein the composition comprises a first and second precursor, the first precursor the second precursor have similar boiling points (b.p.) or the difference between the b.p. of the first precursor and the b.p. of the second precursor is 40° C. or less, 30° C. or less, or 20° C. or less, or 10° C. Alternatively, the difference between the boiling of the first and second precursors ranges from any one or more of the following end-points: 0, 10, 20, 30, or 40° C. Examples of suitable ranges of b.p. difference include without limitation, 0 to 40° C., 20° to 30° C., or 10° to 30° C. In these embodiments, the first and the second precursors can be delivered via direct liquid injection, vapor draw or bubbling while still keeping the same liquid ratio in the gas phase.

In embodiments wherein the composition comprises a first and second precursor, the amount of first precursor in the composition, by weight percentage of the overall composition, ranges from 0.5% by weight to 99.5% or from 10% by weight to 75% with the balance being the second precursor or any additional precursors added thereto. In these or other embodiments, the amount of second precursor in the composition by weight percentage ranges from 0.5% by weight to 99.5% or from 10% by weight to 75% with the balance being the first precursor(s) or any additional precursors. In an alternative embodiment, the composition comprises 100% of the first precursor.

One embodiment of the present invention is related to a precursor formulation consisting of an organoaminosilane with a formula of $Si(NR^1R^2)H_3$ and an organoaminoalkylsilane with a formula of $R^5Si(NR^3R^4)_xH_{3-x}$ wherein $R^{1-4}$ are selected from the group consisting of $C_1$ to $C_{10}$ linear or branched alkyl, alkyl containing other elements such as oxygen or nitrogen, cyclic alkyl, alkenyl, alkynyl, aromatic hydrocarbon; $R^5$ is selected from the group consisting of $C_1$ to $C_{10}$ linear or branched alkyl, alkyl containing oxygen or nitrogen, cyclic alkyl, alkenyl, alkynyl, aromatic hydrocarbon, Cl, Br, and I; $R^1$ and $R^2$ can form a cyclic or alkyl substituted cyclic ring; $R^3$ and $R^4$ can also form a cyclic or alkyl substituted cyclic ring; x=1, 2, 3. Preferably, $R^{1-2}$ and $R^{3-4}$ are independently selected from the same $C_1$ to $C_{10}$ linear or branched alkyls.

Table I provides exemplary compositions comprising both first and second precursors wherein the first precursor comprises an organoaminoalkylsilane of the formula $R^5Si(NR^3R^4)_xH_{3-x}$ wherein x=1, 2, 3 and wherein Me (methyl), Et (ethyl), $^n$Pr (normal propyl), $^i$Pr (iso-propyl), $^n$Bu (normal butyl), $^i$Bu (iso-butyl), $^s$Bu (secondary butyl), and $^t$Bu (tertiary butyl) and the optional second precursor comprises an organoaminosilane having the following general formula $Si(NR^1R^2)H_3$. In these or other embodiments, the exemplary compositions may be provided in a stainless steel vessel, such as without limitation, a pressurizable vessel for storage and delivery to the reactor. In this or other embodiments, the vessel is fitted with the proper valves and fittings to allow the delivery of the first and second precursor to the reactor for a CVD or an ALD process. In certain embodiments, such vessels can also have means for mixing the first and optional second precursors, if present, or can be premixed. Alternatively, the first and optional second precursors can be maintained in separate vessels or in a single vessel having separation means for maintaining the precursors in the composition separate during storage.

TABLE I

Exemplary Precursor Compositions

| No. | First Precursor | Optional Second Precursor |
|---|---|---|
| 1. | $(^iPr_2N)R^5SiH_2$ wherein $R^5$ is selected from the group consisting of Me (methyl), Et (ethyl), $^n$Pr (normal propyl), $^i$Pr (iso-propyl), $^n$Bu (normal butyl), $^i$Bu (iso-butyl), $^s$Bu (secondary butyl), $^t$Bu (tertiary butyl), isomers of pentyl, vinyl, phenyl, and alkyl substituted phenyl | $(^iPr_2N)SiH_3$ |
| 2. | $(^sBu_2N)R^5SiH_2$ wherein $R^5$ is selected from the group consisting of Me, Et, $^n$Pr, $^i$Pr, $^n$Bu, $^i$Bu, $^s$Bu, $^t$Bu, isomers of pentyl, vinyl, phenyl, and alkyl substituted phenyl | $(^sBu_2N)SiH_3$ |
| 3. | (2,6-dimethylpiperidino)$R^5SiH_2$ wherein $R^5$ is selected from the group consisting of Me, Et, $^n$Pr, $^i$Pr, $^n$Bu, $^i$Bu, $^s$Bu, $^t$Bu, isomers of pentyl, vinyl, phenyl, and alkyl substituted phenyl | (2,6-dimethylpiperidino)$SiH_3$ |
| 4. | (phenylmethylamino)$R^5SiH_2$ wherein $R^5$ is selected from the group consisting of Me, Et, $^n$Pr, $^i$Pr, $^n$Bu, $^i$Bu, $^s$Bu, $^t$Bu, isomers of pentyl, vinyl, phenyl, and alkyl substituted phenyl | (phenylmethylamino)$SiH_3$ |

The method used to form the silicon-containing silicon containing films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposit films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the silicon containing film is deposited using an ALD process. In another embodiment, the silicon containing film is deposited using a CCVD process. In a further embodiment, the silicon containing film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursor(s) prior to and/or during the introduction to the reactor. In this connection, deposition techniques such as ALD or CCVD processes are used to deposit the carbon-doped silicon containing film. In one embodiment, the film is deposited via an ALD process by exposing the substrate surface alternatively to the one or more the first precursor, oxygen source if an oxide film, nitrogen-containing source if a nitride film, second precursor, or other precursor or reagent. Film growth proceeds by self-limiting control of surface reaction, the pulse length of each precursor or reagent, and the deposition temperature. However, once the surface of the substrate is saturated, the film growth ceases.

As previously mentioned, in certain embodiments, such as for depositing a carbon-doped silicon containing film such as a silicon oxide or a silicon nitride film using an ALD, CCVD (PECCVD), or PEALD deposition method, the compositions described herein may be able to deposit films at relatively low deposition temperatures, e.g., of 500° C. or less, or 400° C. or less, 300° C. or less, 200° C. or less, 100° C. or less, or 50° C. or less or room temperature. In these or other embodiments, the substrate (deposition) temperature ranges from any one or more of the following end-points: 0, 25, 50, 100, 200, 300, 400, or 500° C. Examples of these ranges are, without limitation, 0 to 100° C., 25 to 50° C., 100° to 300° C., or 100° C. to 500° C. In one particular embodiment, the deposition temperature is below 200° C. which allows carbon to be incorporated into the resulting films, providing films such as carbon doped silicon oxide with low etching rate.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing and/or organoaminosilane precursor may be introduced into the reactor for a predetermined time period. In certain embodiments, the time period ranges from about 0.001 to about 500 seconds.

In certain embodiments, the silicon containing films deposited using the methods described herein is formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), water plasma, oxygen ($O_2$), peroxide ($O_3$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited silicon containing film.

In certain embodiments, the silicon containing films comprise silicon and nitrogen. In these embodiments, the silicon containing films deposited using the methods described herein are formed in the presence of nitrogen-containing source. A nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursor(s), oxygen source, the nitrogen-containing source, and/or other precursors, source gases, and/or reagents may be performed by changing the time for supplying them to change the stoichiometric composition of the resulting silicon containing film.

Energy is applied to the at least one of the precursor, nitrogen-containing oxygen-containing source, reducing agent, other precursors or combination thereof to induce reaction and to form the silicon containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminosilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations or compositions, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In another embodiment, a vessel for depositing a silicon containing film comprising the composition comprising, consisting essentially of, or consisting of, the first and optionally second precursors are described herein. In one particular embodiment, the vessel comprises at least one pressurizable vessel (preferably of stainless steel) fitted with the proper valves and fittings to allow the delivery of the first and second precursor to the reactor for a CVD or an ALD process. In this or other embodiments, the first and optionally second precursors are provided in a pressurizable vessel comprised of stainless steel and the purity of the precursor is 98% by weight or greater or 99.5% or greater which is suitable for the majority of semiconductor applications. In certain embodiments, such vessels can also have means for mixing the first and optional second precursors, if present, or can be premixed. Alternatively, the first and optional second precursors can be maintained in separate vessels or in a single vessel having separation means for maintaining the precursors in the composition separate during storage.

As previously mentioned, the purity level of the precursor(s) in the composition is sufficiently high enough to be acceptable for reliable semiconductor manufacturing. In certain embodiments, the precursors described herein comprise less than 2% by weight, or less than 1% by weight, or less than 0.5% by weight of one or more of the following impurities: free amines, halides, and higher molecular weight species. Higher purity levels of the precursors described herein can be obtained through one or more of the following processes: purification, adsorption, and/or distillation.

In certain embodiments, the gas lines connecting from the precursor canisters to the reaction chamber are heated to one or more temperatures depending upon the process requirements and the container or containers (depending upon whether the first and optionally second precursors (in certain embodiments) are delivered separately or together) is kept at one or more temperatures for bubbling. In other embodiments, a solution comprising the first and optionally second precursor (depending upon whether the first and, if present optionally second, precursors are delivered separately or together) is injected into a vaporizer kept at one or more temperatures for direct liquid injection.

A flow of argon and/or other gas may be employed as a carrier gas to help deliver the vapor of the precursors to the reaction chamber during the precursor pulsing. In certain embodiments, the reaction chamber process pressure is about 1 Torr.

In a typical ALD or CCVD process, the substrate such as a silicon oxide substrate is heated on a heater stage in a reaction chamber that is exposed to the silicon-containing precursor initially to allow the complex to chemically adsorb onto the surface of the substrate.

A purge gas such as argon purges away unabsorbed excess complex from the process chamber. After sufficient purging, a nitrogen-containing source may be introduced into reaction chamber to react with the absorbed surface followed by another gas purge to remove reaction by-products from the chamber. The process cycle can be repeated to achieve the desired film thickness.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon containing film.

In certain embodiments, the method to deposit the carbon-doped silicon-containing film is an ALD or cyclic CVD method and the composition comprises a first and second precursor. In these or other embodiments, the order of the first and second precursor can be delivered in any one or more of the following manners wherein A refers to the delivery of the first precursor and B refers to the delivery of the second precursor: ABABABAB . . . wherein the first and second precursors are alternated until the desired number of cycles are completed; AAAAABBBBB . . . wherein the first precursor is introduced for the first half of the process cycles and the second precursor is introduced for the second half of the process cycles; and combinations thereof. In these or other embodiments, the number of process cycles of the first precursor relative to the second precursor can be optimized to allow for a gradient of carbon within the carbon-containing silicon film.

The method disclosed herein forms the carbon doped silicon oxide films using a precursor composition and an oxygen source. In one particular embodiment, the method comprises the following steps:

Step 1. Contacting vapors generated from a composition comprising an first precursor comprising an organoalkoxyalkylsilane, and optionally a second precursor comprising an organoaminosilane, with a substrate to chemically sorb the precursors on the heated substrate;

Step 2. Purging away any unsorbed precursors;

Step 3. Introducing an oxygen source on the heated substrate to react with the sorbed precursors; and, Step 4. Purging away any unreacted oxygen source.

The steps 1 through 4 are repeated until a desired thickness is achieved.

In another embodiment, the method comprises the following steps:

Step 1. Contacting vapors generated from a first precursor with a substrate to chemically sorb the precursor on the heated substrate, the first precursor which is at least one compound selected from the compounds having the following formulas:

(a)

(b)

(c)

wherein $R^3$, $R^4$, and $R^7$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; $R^5$ and $R^6$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group, and a halide atom; $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; wherein $R^3$ and $R^4$ can form a cyclic ring or an alkyl-substituted cyclic ring; and wherein $R^{10}$ and $R^{11}$ can form a cyclic ring or an alkyl-substituted cyclic ring; L=Cl, Br, I;

Step 2. Purging away any unsorbed precursors;

Step 3. Introducing an oxygen source on the heated substrate to react with the sorbed silicon precursor;

Step 4. Purging away any unreacted oxygen source;

Step 5. Optionally contacting vapors generated from an optional second precursor with a substrate to chemically sorb the second precursor on the heated substrate, wherein the second precursor compound has the formula $Si(NR^1R^2)H_3$ wherein $R^1$ and $R^2$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group and wherein $R^1$ and $R^2$ can form a cyclic ring or an alkyl-substituted cyclic ring;

Step 6. Purging away any unsorbed precursors;

Step 7. Introducing an oxygen source on the heated substrate to react with the sorbed silicon precursor;

Step 8. Purging away any unreacted oxygen source.

The steps 1 through 8 are repeated until a desired thickness is achieved.

In certain embodiments, the carbon-doped silicon containing films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the carbon-doped silicon containing film that is formed using the precursor compositions and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to about 50%; and H ranges from about 0% to about 50% atomic percent weight % wherein x+y+z+v+w=100 atomic weight percent, as determined, for example, by XPS or other means.

As mentioned previously, the method described herein may be used to deposit a carbon-doped silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN and transparent amorphous oxide semiconductor (TAOS) or metal oxide materials include a-IGZO (amorphous gallium indium zinc oxide), zinc oxide. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nano-electromechanical systems, thin film transistor (TFT), and liquid crystal displays (LCD).

The following examples illustrate the method for preparing organoaminosilane precursors as well as deposited silicon-containing films described herein and are not intended to limit it in any way.

EXAMPLES

Example 1: Preparation of
2,6-dimethylpiperidino(methyl)silane 2,6-dimethylpiperidino(chloro)silane was prepared by dissolving 0.052 $Nm^3$ of dichlorosilane in 4.36 L of hexanes in a 6 L stirred reactor at −20° C. under a nitrogen atmosphere. To this solution was added 244 g of triethylamine and then 260 g of cis-2,6-dimethylpiperidine was added slowly with continuous agitation while maintaining the temperature at −20° C. Once the addition was complete, the mixture was allowed to warm to 20° C. and stirred for 16 h. A voluminous white precipitate formed, which was removed by filtration. The precipitate was rinsed with hexane. The filtrate combined with the rinses contained 2,6-dimethylpiperidino(chloro)silane, which was isolated by stripping at reduced pressure to remove the hexanes. Further purification was obtained by simple distillation of the residue at 100° C. under reduced pressure. The identity of 2,6-dimethylpiperidino(chloro)silane was determined by mass spectrometry which showed peaks at 177 (M+), 162 (M-$CH_3$) which are consistent with the molecular weight (177.75) of 2,6-dimethylpiperidino(chloro)silane.

A 130 g of 2,6-dimethylpiperidino(chloro)silane prepared as described above was dissolved in 386 g of tetrahydrofuran and placed in a 2 L reactor under an inert atmosphere. The solution was chilled to −20° C. and then 247 g of 3 molar methylmagnesium chloride solution in tetrahydrofuran was added gradually with stirring over 60 minutes while maintaining the temperature at −20° C. The mixture was then allowed to warm to 20° C. over 30 minutes and then allowed to stir at that temperature for 18 h. A heavy white precipitate was observed. The mixture was filtered and the precipitate was rinsed with an additional 100 mL of tetrahydrofuran. The tetrahydrofuran from these combined filtrates was removed by simple distillation at reduced pressure. The resulting yellow slurry was extracted with 400 mL of hexanes and the solids were removed by filtration and rinsed with two portions of 50 mL of hexanes. The hexanes were stripped from this combined filtrate to produce crude product that was further purified by simple distillation to provide 70.4 g of product. The identity of the material was determined by mass spectrometry (see FIG. 2), which showed peaks at 157 (M+), 142 (M-$CH_3$ and are consistent with the molecular weight (157.33) of 2,6-dimethylpiperidinomethylsilane. Gas chromatography with thermal conductivity detection indicates a purity of approximately 97% by weight. The boiling point was measured by DSC to be ~173° C. at atmospheric pressure (see FIG. 2).

Figure 2:
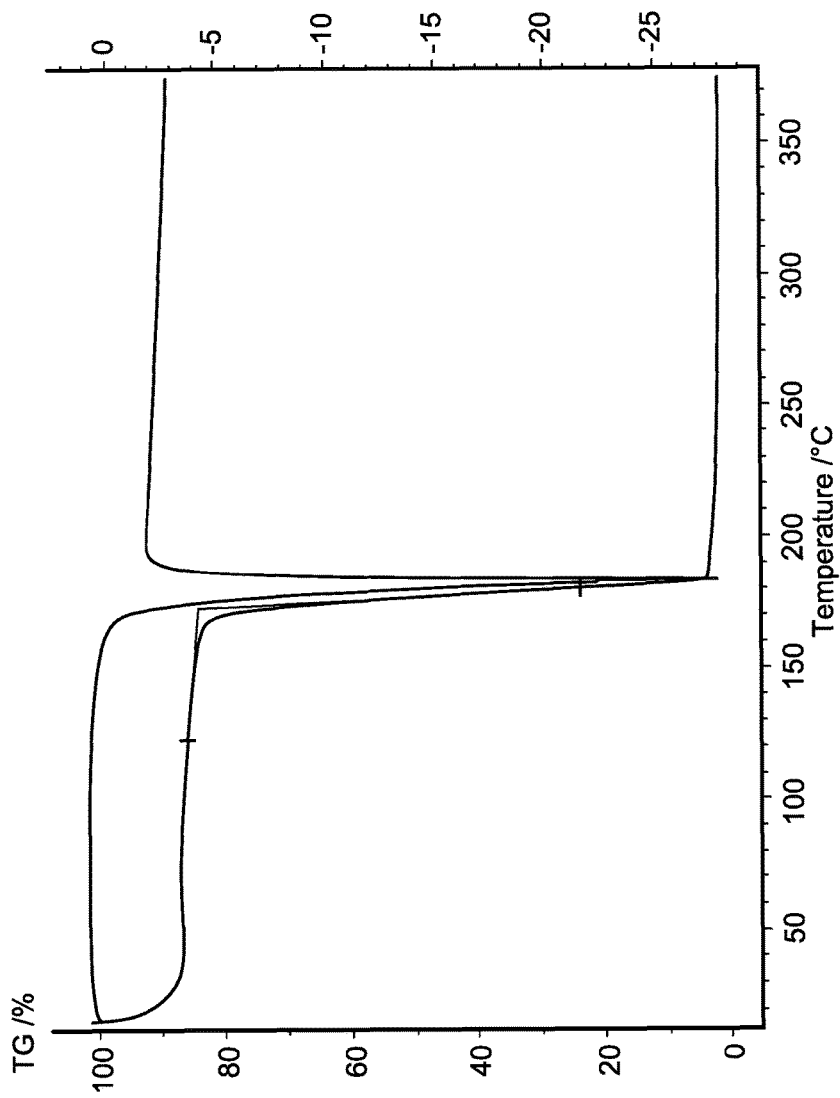
FIG. 2 provides the thermal gravimetric analysis (TGA) and differential scanning calorimetry (DCS) analysis of 2,6-dimethylpiperidinomethylsilane.

Three 10 cc stainless steel containers were carefully washed and baked out at 175° C. prior to use. Each was loaded with an ampoule containing a 2 ml sample of 2,6-dimethylpiperidinomethylsilane. The ampoules were then stored in constant temperature environments using laboratory ovens pre-set at 100° C.±2° C. for three days. The samples were evaluated by gas chromatography (GC) to determine the extent of degradation and the results are shown in FIG. 2. The average purity after heating showed virtually no change, demonstrating it has excellent thermal stability and can be employed as a suitable precursor for reliable semi-conductor processes.

Example 2: Atomic Layer Deposition of
Silicon-Containing Films

Atomic layers depositions of silicon-containing films were conducted using the following precursors: 2,6-dimethylpiperidinosilane and 2,6-dimethylpiperidinomethylsilane. The depositions were performed on a laboratory scale ALD processing tool. All gases (e.g., purge and reactant gas or precursor and oxygen source) were preheated to 100° C. prior to entering the deposition zone. Gases and precursor flow rates were controlled with ALD diaphragm valves having high speed actuation. The substrates used in the deposition were 12 inch length silicon strips having thermocouples attached on a sample holder to confirm the substrate temperature. Depositions were performed using ozone as the oxygen source gas and the process parameters of the depositions are provided in Table II.

TABLE II

Process for Atomic Layer Deposition of Silicon-containing Films with Ozone

| Step | Time | Action | Flow/Pressure | Description |
|---|---|---|---|---|
| Step 1 | 6 seconds (sec) | Nitrogen Purge of Reactor | Flow 1.5 slpm $N_2$ | Purges out unreacted chemical from reactor |
| Step 2 | 6 sec | Chamber evacuation | <100 mT | Prepare the reactor for the precursor dose |
| Step 3 | 2 sec | Close throttle valve | | Increases precursor resonance time |
| Step 4 | Variable | Dose Organo-aminosilane Precursor | | Reactor pressure typically <1 T during dose |
| Step 5 | 6 sec | Nitrogen Purge of Reactor | Flow 1.5 slpm $N_2$ | Purges out unreacted chemical from reactor |
| Step 6 | 6 sec | Chamber evacuation | <100 mT | Prepare the reactor for the organoaminosilane precursor dose |
| Step 7 | 2 sec | Close throttle valve | | Increases the organoaminosilane precursor resonance time |
| Step 8 | 4 sec | Dose Ozone | | $O_3$ at 18-20% post generator, P = <8 T |

The resultant silicon-containing films were characterized for deposition rate and refractive index. Thickness and refractive indices of the films was measured using a FilmTek 2000SE ellipsometer by fitting the reflection data from the film to a pre-set physical model (e.g., the Lorentz Oscillator model).

Wet etch rate was performed using 1% solution of 49% hydrofluoric (HF) acid in deionized water. Thermal oxide wafers were used as reference for each test. Films thickness of both samples and comparative silicon oxide reference were measured with ellipsometer before and after etch. Silicon oxide films with carbon dopant have lower wet etch rate than silicon oxide films.

Film composition was analyzed with dynamic secondary ions mass spectrometry (SIMS) technique. Fourier Transform Infrared (FTIR) spectrometry is used to confirm film structure. Absorbance in IR spectra is normalized with film thickness for comparison. Table III is summary of the deposition temperature, deposition rate, refractive index, wet etch rate and carbon content measured by the Dynamic Secondary Ion Mass Spectroscopy (SIMS). The silicon-containing films were deposited using the following methods described below.

Method (a) describes the formation of silicon-containing films using 2,6-dimethylpiperidinosilane at three different substrate temperatures: 300° C., 150° C. and 100° C. using the following process steps:
Step 1. Contacting vapors of 2,6-dimethylpiperidinosilane
Step 2. Purging away any unsorbed 2,6-dimethylpiperidinosilane
Step 3. Introducing ozone to react with the sorbed 2,6-dimethylpiperidinosilane
Step 4. Purging away any unreacted ozone
The above steps for Method (a) were repeated 500 times. The deposited films do not show any significant C—H signatures at 2800-2960 $cm^{-1}$ or Si—$CH_3$ peak at ~1250 $cm^{-1}$, as confirmed with FTIR.

Method (b) describes the formation of silicon-containing films using 2,6-dimethylpiperidinomethylsilane at three different substrate temperatures: 300° C., 150° C. and 100° C. using the following process steps:
Step 1. Contacting vapors of 2,6-dimethylpiperidinomethylsilane
Step 2. Purging away any unsorbed 2,6-dimethylpiperidinomethylsilane
Step 3. Introducing ozone to react with the sorbed 2,6-dimethylpiperidinomethylsilane
Step 4. Purging away any unreacted ozone
The steps were repeated for 500 cycles. Film deposited at 300° C. showed a very similar IR signature as the 2,6-dimethylpiperidinosilane in Method (a) (e.g., no C—H signatures at 2800-2960 $cm^{-1}$ and Si—$CH_3$ signature at ~1250 $cm^{-1}$). Both C—H and Si—$CH_3$ absorbance peaks occurred in films deposited at 150° C. and stronger at 100° C.

Method (c) describes the formation of silicon-containing films using alternating doses of the first precursor 2,6-dimethylpiperidinomethylsilane and the second precursor 2,6-dimethylpiperidinosilane at a substrate temperature of 100° C.;
Step 1. Contacting vapors of 2,6-dimethylpiperidinosilane
Step 2. Purging away any unsorbed 2,6-dimethylpiperidinosilane
Step 3. Introducing ozone to react with the sorbed 2,6-dimethylpiperidinosilane
Step 4. Purging away any unreacted ozone
Step 5. Contacting vapors of 2,6-dimethylpiperidinomethylsilane
Step 6. Purging away any unsorbed 2,6-dimethylpiperidinomethylsilane;
Step 7. Introducing ozone to react with the sorbed 2,6-dimethylpiperidinomethylsilane
Step 8. Purging away any unreacted ozone
The steps were repeated for 250 times.

TABLE III

Summary of Resulting Silicon-containing Films using Methods (a) through (c)

| Precursor | Deposition temperature (° C.) | Deposition rate (Å/cycle) | Refractive index | Wet etch rate (Å/min) | Carbon Content (# of atoms/cc) |
|---|---|---|---|---|---|
| 2,6-dimethylpiperidinosilane (Method (a)) | 300 | 1.86 | 1.455 | 5.43 | $2 \times 10^{19}$ |
| 2,6-dimethylpiperidinosilane (Method (a)) | 150 | 1.96 | 1.464 | 5.25 | $6 \times 10^{19}$ |
| 2,6-dimethylpiperidinosilane (Method (a)) | 100 | 1.90 | 1.465 | 5.78 | $1 \times 10^{20}$ |
| 2,6-dimethylpiperidinomethylsilane (Method (b)) | 300 | 1.24 | 1.473 | 5.13 | $2 \times 10^{19}$ |
| 2,6-dimethylpiperidinomethylsilane (Method (b)) | 150 | 0.58 | 1.513 | 3.07 | $3 \times 10^{21}$ |

TABLE III-continued

Summary of Resulting Silicon-containing Films using Methods (a) through (c)

| Precursor | Deposition temperature (° C.) | Deposition rate (Å/cycle) | Refractive index | Wet etch rate (Å/min) | Carbon Content (# of atoms/cc) |
|---|---|---|---|---|---|
| 2,6-dimethylpiperidinomethylsilane (Method (b)) | 100 | 0.57 | 1.517 | 1.18 | $2 \times 10^{22}$ |
| 2,6-dimethylpiperidinosilane and 2,6-dimethylpiperidinomethylsilane (Method (c)) | 100 | 1.57 | 1.464 | 2.43 | $6 \times 10^{21}$ |

Referring to Table III, the wet etch rates for silicon-containing films using 2,6-dimethylpiperidinosilane showed no improvement regardless of deposition temperatures which is consistent with no carbon incorporation into the films. However, unexpectedly, silicon-containing films deposited at 300° C. using 2,6-dimethylpiperidinomethylsilane shows very similar IR signature as the films from 2,6-dimethylpiperidinosilane, i.e. no C—H signatures at 2800-2960 cm$^{-1}$ and Si—CH$_3$ signature at ~1250 cm$^{-1}$, although it was hoped that the Si—CH$_3$ group in 2,6-dimethylpiperidinomethylsilane would be incorporated into the resulting silicon-containing films. Further, both C—H and Si—CH$_3$ absorbance peaks occurred in films deposited at 150° C. and were stronger at 100° C. in films deposited with dimethylpiperidinomethylsilane. The wet etch rate is directly correlated with the amount of carbon incorporated into the films, i.e. the higher the carbon content, the lower the wet etch rate. The carbon content in the films deposited at 300° C. using either 2,6-dimethylpiperidinosilane or 2,6-dimethylpiperidinomethylsilane deposited were very similar at 2×10$^{19}$ atoms/cc, indicating that the ozone effectively oxidized the Si—CH$_3$ group in 2,6-dimethylpiperidinomethylsilane. However, lowering the deposition temperature from 300° C. to 150° C. or 100° C. increased the carbon incorporation into films due to less effective oxidation of organoaminosilanes. Importantly, the effect is more pronounced for films deposited from 2,6 dimethylpiperidinomethylsilane at temperature of 100° C., showing two orders of magnitude more carbon atoms. Additionally, not to be bound by theory, it is speculated that the amount of carbon in the films can also be adjusted by several other methods such as decreasing ozone pulse time, decreasing ozone concentration, alternating layers of carbon doped silicon containing film as well as co-depositing carbon doped silicon containing layer with non-carbon doped silicon containing films.

Figure 3:
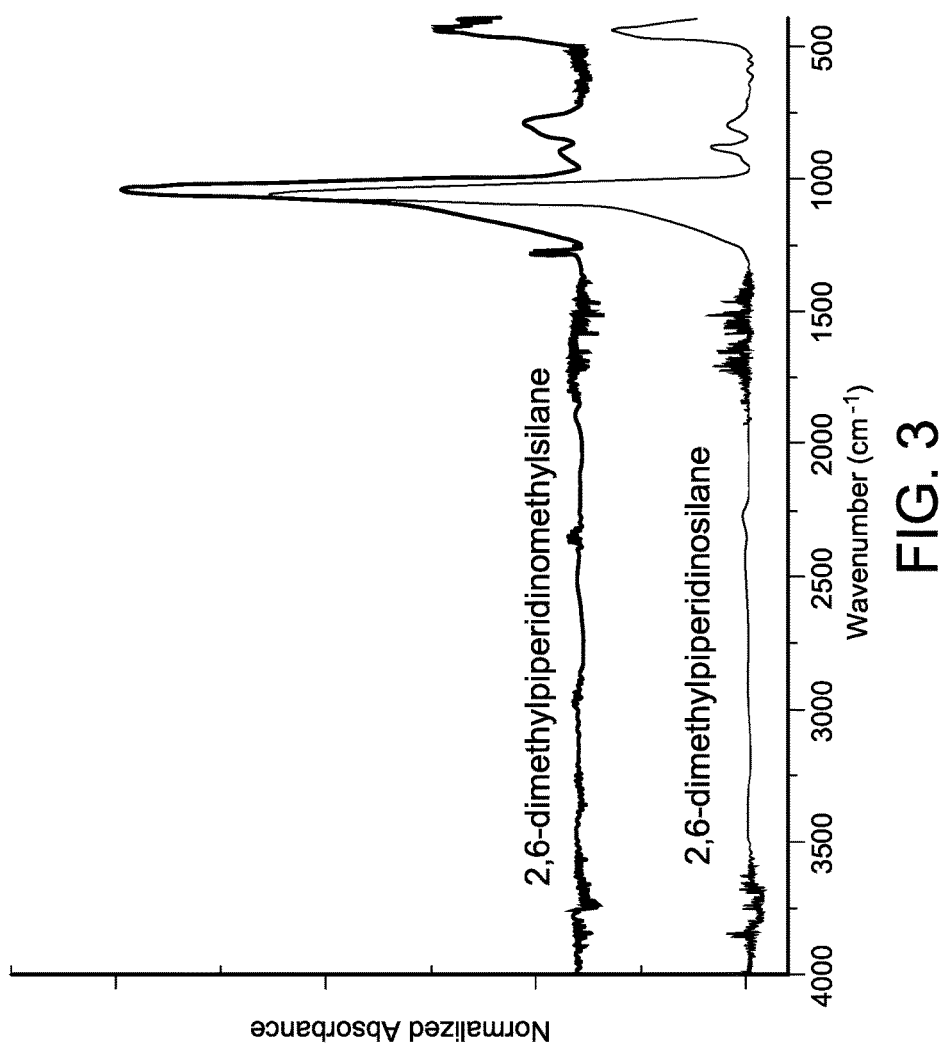
FIG. 3 provides an IR spectra comparison of films deposited using 2,6-dimethylpiperidinosilane and 2,6-dimethylpiperidinomethylsilane at a temperature of 100° C.
Figure 4:
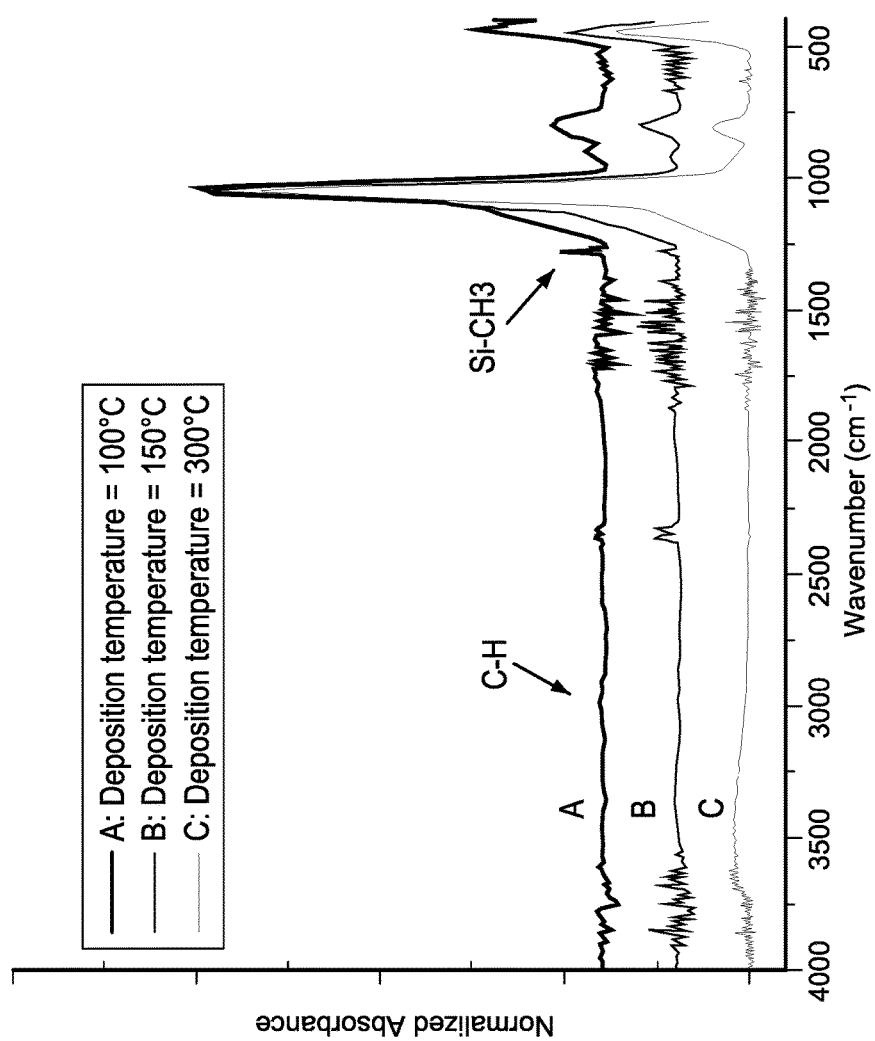
FIG. 4 provides an IR spectra comparison of films deposited using 2,6-dimethylpiperidinomethylsilane at different temperatures (e.g., 100° C., 150° C., and 300° C.).

FIG. 3 shows the IR spectra comparison between 2,6-dimethylpiperidinosilane and 2,6-dimethylpiperidinomethylsilane deposited at 100° C. FIG. 5 provides a comparison among 2,6-dimethylpiperidinomethylsilane films deposited at different temperatures. This example demonstrates that the carbon content of the silicon-containing can be tuned via varying deposition temperature or using two different organoaminosilanes.

The invention claimed is:

1. A composition for depositing a carbon-doped silicon containing film comprising:
a precursor comprising at least one organoaminosilane having a formula of $R^8N(SiR^9(NR^{10}R^{11})H)_2$,
wherein $R^8$ and $R^9$ are each independently selected from the group consisting of hydrogen, $C_1$ to $C_{10}$ linear or branched alkyl, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; and $R^{10}$ and $R^{11}$ are each independently selected from the group consisting of a $C_1$ to $C_{10}$ linear or branched alkyl group, a $C_3$ to $C_{10}$ cyclic alkyl group, a linear or branched $C_2$ to $C_{10}$ alkenyl group, a linear or branched $C_2$ to $C_{10}$ alkynyl group, a $C_5$ to $C_{10}$ aromatic group, and a $C_3$ to $C_{10}$ saturated or unsaturated heterocyclic group; wherein $R^{10}$ and $R^{11}$ can form a cyclic ring or an alkyl-substituted cyclic ring; and L=Cl, Br, I.

2. The composition of claim 1 comprising $R^8N(SiR^9(NR^{10}R^{11})H)_2$ wherein $R^8$ is selected from the group consisting of Me, Et, "Pr, $^i$Pr, " Bu, $^i$Bu, $^s$Bu, $^t$Bu, isomers of pentyl, vinyl, phenyl, and alkyl substituted phenyl.

3. The composition of claim 1 comprising $R^8N(SiR^9(NR^{10}R^{11})H)_2$ wherein $R^9$ is selected from the group consisting of hydrogen, Me, Et, "Pr, $^i$Pr, " Bu, $^i$Bu, $^s$Bu, $^t$Bu, isomers of pentyl, vinyl, phenyl, and alkyl substituted phenyl.

4. The composition of claim 1 comprising $R^8N(SiR^9(NR^{10}R^{11})H)_2$ wherein $R^{10}$ and $R^{11}$ are independently selected from the group consisting of Me, Et, "Pr, $^i$Pr, " Bu, $^i$Bu, $^s$Bu, $^t$Bu, isomers of pentyl, vinyl, phenyl, and alkyl substituted phenyl.

* * * * *